United States Patent [19]
Dale et al.

[11] Patent Number: 5,879,920
[45] Date of Patent: Mar. 9, 1999

[54] COATED ENZYME-CONTAINING GRANULE

[75] Inventors: Douglas A. Dale, Pacifica; Alfred L. Gaertner, San Bruno, both of Calif.; Gene Park, Cincinnati, Ohio; Nathaniel T. Becker, Burlingame, Calif.

[73] Assignee: Genencor International, Inc., Rochester, N.Y.

[21] Appl. No.: 577,894

[22] Filed: Dec. 22, 1995

Related U.S. Application Data

[63] Continuation-in-part of Ser. No. 417,714, Apr. 6, 1995, abandoned, which is a continuation of Ser. No. 210,975, Mar. 21, 1994, abandoned, which is a continuation of Ser. No. 957,973, Oct. 7, 1992, Pat. No. 5,324,649, which is a continuation-in-part of Ser. No. 772,510, Oct. 7, 1991, abandoned.

[51] Int. Cl.$^6$ .............................. C12N 9/98; C12N 11/08; C11D 10/00; D06M 16/00
[52] U.S. Cl. .......................... 435/187; 435/175; 435/176; 435/177; 435/180; 435/182; 435/264; 510/320; 510/530
[58] Field of Search ...................... 435/174, 175, 435/176, 177, 178, 179, 180, 182, 187, 264; 510/320, 530

[56] References Cited

U.S. PATENT DOCUMENTS

| | | | |
|---|---|---|---|
| 3,798,128 | 3/1974 | Minato et al. | 195/68 |
| 4,009,076 | 2/1977 | Green et al. | 195/63 |
| 4,016,040 | 4/1977 | Win et al. | 195/68 |
| 4,106,991 | 8/1978 | Markussen et al. | 195/63 |
| 4,689,297 | 8/1987 | Good et al. | 435/174 |
| 4,707,287 | 11/1987 | Herdeman | 252/91 |
| 4,740,469 | 4/1988 | Nishinaka | 435/187 |
| 4,759,956 | 7/1988 | Amer et al. | 427/213 |
| 4,876,198 | 10/1989 | Markussen | 435/183 |
| 4,898,781 | 2/1990 | Onouchi et al. | 408/402.22 |
| 4,940,665 | 7/1990 | Lijima et al. | 435/187 |
| 4,973,417 | 11/1990 | Falholt | 252/95 |
| 5,108,457 | 4/1992 | Poulose et al. | 8/111 |
| 5,225,102 | 7/1993 | Coyne et al. | 252/186.26 |
| 5,324,649 | 6/1994 | Arnold et al. | 435/187 |

FOREIGN PATENT DOCUMENTS

| | | |
|---|---|---|
| 0193829 | 9/1986 | European Pat. Off. |
| 0277532 | 8/1988 | European Pat. Off. |
| 0293055 | 11/1988 | European Pat. Off. |
| 0304332 | 2/1989 | European Pat. Off. |
| 0320483 | 6/1989 | European Pat. Off. |
| 61-162185 | 7/1986 | Japan. |

*Primary Examiner*—David M. Naff
*Attorney, Agent, or Firm*—Kirsten A. Anderson

[57] ABSTRACT

A granular enzyme composition is produced having reduced tendency to form dust and leave a residue, and improved stability and delayed release characteristics. The composition has a core, optionally coated with a vinyl polymer, a layer containing an enzyme and a vinyl polymer and optionally a plasticizer or anti-agglomeration agent, and an outer coating containing a polymer and optionally a low residue pigment and/or lubricant. Preferably, the core is a salt or sugar nonpareil, the vinyl polymer coating the core is polyvinyl alcohol and most preferably partially hydrolyzed polyvinyl alcohol, the vinyl polymer in the enzyme layer is polyvinyl pyrrolidone, and the polymer of the outer coating is polyvinyl pyrrolidone, polyvinyl alcohol which may be partially hydrolyzed, polyethylene glycol or mixtures thereof such as a mixture of polyvinyl pyrrolidone and polyvinyl alcohol or a mixture of polyvinyl pyrrolidone and polyethylene glycol. Preferably, the pigment is titanium dioxide and the lubricant is a nonionic or anionic surfactant such as a linear primary alcohol of a 9–15 carbon atom chain length alkane or alkene or an ethoxylate or ethoxysulfate derivative thereof. The enzyme can be a protease, amylase, lipase, cellulase, xylanase, oxidase, peroxidase or mixtures thereof. The composition may be produced by spray coating in a fluidized bed a solution of the enzyme and vinyl polymer onto the core to form the enzyme layer, and then spray coating in a fluidized bed a solution of polymer on the enzyme layer to form the outer coating.

20 Claims, 4 Drawing Sheets

COATED ENZYME-CONTAINING GRANULE

CROSS REFERENCE TO RELATED APPLICATIONS

This application is a continuation-in-part of U.S. application Ser. No. 08/417,714, filed Apr. 6, 1995 (abandoned), which is a continuation of U.S. application Ser. No. 08/210,975, filed Mar. 21, 1994 (abandoned), which is a continuation of U.S. application Ser. No. 07/957,973, filed Oct. 7, 1992, now U.S. Pat. No. 5,324,649, which is a continuation-in-part of U.S. application Ser. No. 07/772,510, filed Oct. 7, 1991 (abandoned).

FIELD OF THE INVENTION

This invention relates to improvements in or relating to enzyme granules, as well as improved processes for producing such granules.

BACKGROUND OF THE INVENTION

Recently the use of enzymes, especially of microbial origin, has been more and more common. Enzymes are used in several industries including, for example, the starch industry, the dairy industry and the detergent industry. It is well known in the detergent industry that the use of enzymes, particularly proteolytic enzymes, has created industrial hygiene concerns for detergent factory workers, particularly due to the health risks associated with dustiness of the available enzymes.

Since the introduction of enzymes into the detergent business, many developments in the granulation and coating of enzymes to reduce enzyme dust have been offered by the industry. However, in today's state of ever-increasing environmental concern and heightened awareness of industrial hygiene, there remains a continuing need for low dust enzyme granules. Furthermore, there are additional characteristics desirable in enzyme granules not currently available in known granulation products. Some of these additional characteristics are related to the need to further alleviate industrial hygiene concerns (lower dust granules) while optimizing customer and end-user satisfaction (oxidatively stable and low residue granules) with the product while simultaneously reducing the cost of granulation (improved processing time), thus reducing cost of the overall enzyme product.

Depending on the desired end use of the granule, desirable characteristics may include the need for delayed release of the enzyme, preferably without having to increase the amount of chlorine scavenger additives currently used in granulation techniques. This delayed release has potential benefit, for example, in protecting enzymes from oxidation or autolytic degradation in washing machines until sufficient amounts of stabilizing proteins or peptides are released from dirty clothing into the wash water. Conversely, if the granule is to be used in an automatic dishwashing detergent (ADD), it would be desirable to have quick dissolution of the granule with no residue or film-forming properties on the surface of the dish or glassware in the dishwasher. Additional desirable characteristics include low residue granule formulations (where low residue is defined as a reduced tendency to leave noticeable undissolved residues or filming on clothes or other material such as glassware or plates, etc.). This characteristic is desirable to the customer (end-user) of a detergent or ADD formulation. In addition, improved stability (enhanced shelf life) formulations are needed in the industry. Accomplishing all these desired characteristics simultaneously while maintaining cost containment for the granule production is a particularly challenging task. For example, many potential polymers to delay the release of the enzyme leave behind insoluble residues, which are undesirable to the user, or such polymers cause increased processing time, which causes increased costs. Also, most potential granulating cores, which are attrition-resistant and therefore suitable for producing low dust granules, tend to leave behind insoluble residues.

Therefore, it is an object of the present invention to provide low dust, low residue enzyme granules. These granules preferably have increased stability. It is another object of the present invention to provide processes and enzyme granule compositions which afford the formation of such improved granules in much lower processing time, thus reducing cost of the granular product.

SUMMARY OF THE INVENTION

According to the present invention, there are provided improved enzyme-containing granules, such granules comprising:

a) a core comprising one or more water soluble or dispersible agent(s), said core being optionally coated with a vinyl polymer or vinyl copolymer;

b) an enzyme layer comprising one or more enzyme(s)s and one or more vinyl polymer(s) or copolymer(s); and c) an outer coating comprising one or more polymer(s) or copolymer(s) and, optionally, a low residue pigment and/or a lubricant.

In a preferred embodiment of the enzyme granule of the present invention, the vinyl polymer useful in the core is a polyvinyl alcohol (PVA), most preferably partially hydrolyzed PVA, while the vinyl polymer in the enzyme is polyvinyl pyrrolidone (PVP) and the polymer in the outer coating is PVA, PVP and/or polyethylene glycol (PEG), including mixtures thereof.

In a further preferred embodiment of the present invention, the core material is a nonpareil (sugar or salt) which has been coated with partially hydrolyzed PVA. In another embodiment of the present invention, the coating on the core may comprise additional agents such as a plasticizer.

The enzyme-containing granules of the present invention may comprise any enzyme; however, in a preferred embodiment of the present invention, the enzyme is selected from the group consisting of proteases, amylases, lipases, cellulases (or components thereof) or oxidases, or mixtures thereof.

In a preferred embodiment of the present granule, the enzyme layer comprises a PVP, either alone or in combination with additional agents such as plasticizers or anti-agglomeration agents.

For use in ADD applications where quick dissolution and low filming (low residue) characteristics are necessary, in addition to low dust, the enzyme-containing granules of the present invention preferably comprise an outer coating of PVA, PVP and/or PEG, or mixtures of such polymers. More preferably, the outer coating comprises an integral mixture of PVA and PVP, or a mixture of PVP and PEG, along with a low residue pigment and a lubricant.

This invention also comprises methods for making low dust granules. A method embodiment of the present invention comprises:

a) selecting a core material which is a water soluble or dispersible agent coated with a suitable vinyl polymer such as PVA;

b) coating the core of step a) with one or more enzyme(s) and one or more suitable vinyl polymer(s) or copolymer(s); and c) coating the product of step b) with one or more suitable polymer(s) or copolymer(s), alone or in combination with a low residue pigment or a lubricant, or a mixture thereof.

In a preferred process embodiment of the present invention, the vinyl polymer used in step b) of the process is a PVP and the polymer in step c) is one or more of PVP, PVA or PEG (or mixtures thereof).

In a more preferred embodiment of the present invention, the method comprises selecting a core coated with PVA, utilizing PVP in the enzyme layer, and including PVA, PVP and/or PEG in the outer coating layer. Most preferably, the outer coating layer further comprises a lubricant such as an ionic or nonionic surfactant.

DETAILED DESCRIPTION OF THE INVENTION

Figure 1:
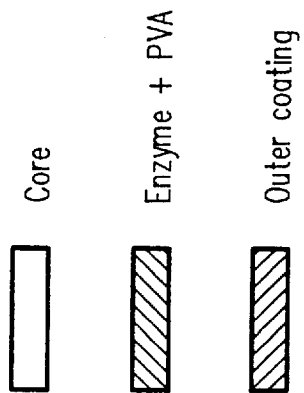
FIG. 1 is a cross-sectional diagram of an enzyme granule.
Figure 1:
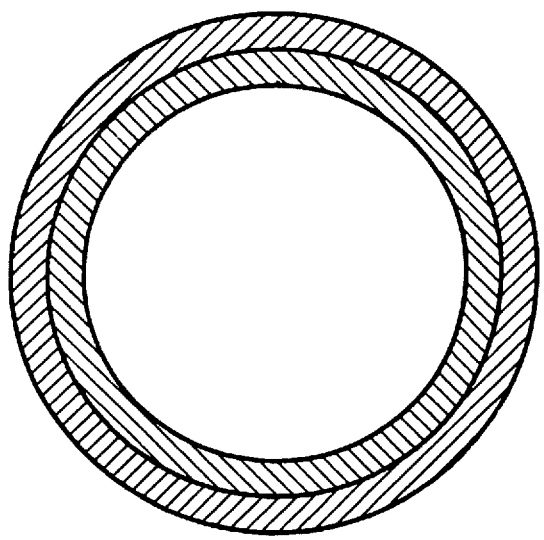
Figure 2:
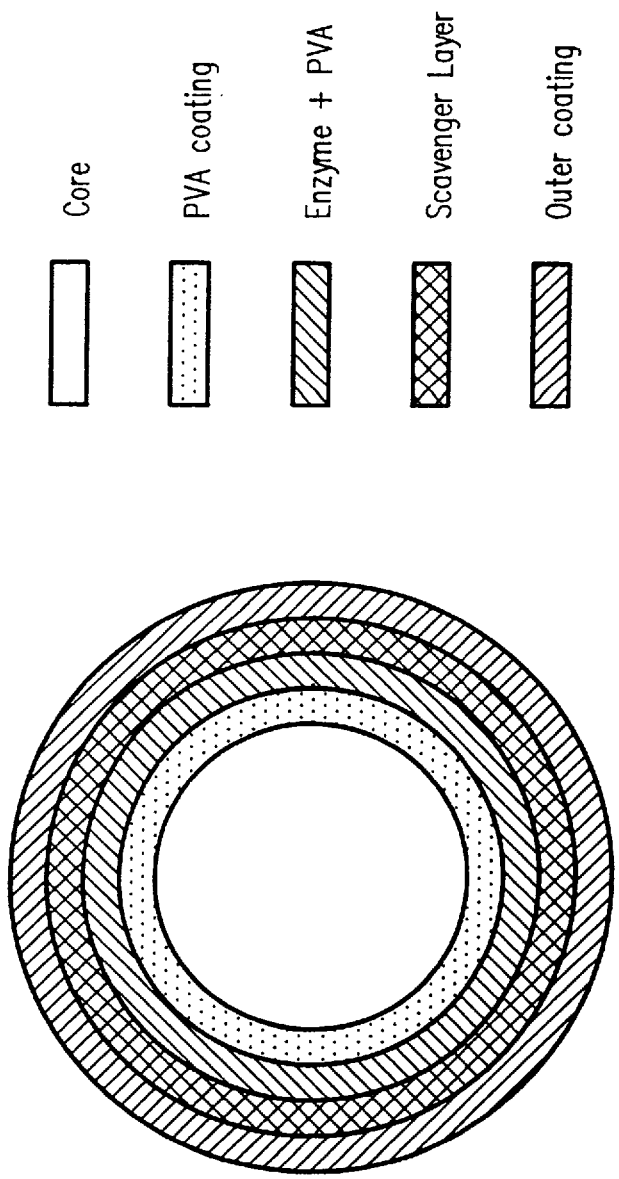
FIG. 2 is a cross-sectional diagram of an enzyme granule comprising additional layers.

Surprisingly, it has been found that the incorporation of a vinyl polymer or copolymer, or a mixture of vinyl polymers and/or other polymers, and preferably PVA, PVP and PEG, in one or more of the granule layers provides a granule having improved characteristics such as low dust, low residue (upon dissolution), altered enzyme release and increased stability. It has also been found that such improved granules can be made in a much reduced processing time.

A preferred vinyl polymer useful in the present invention is polyvinyl alcohol (PVA), which is defined as a homopolymer or copolymer in which vinyl acetate is a starting monomer unit and in which most or all (70–100%) of the acetate moieties are subsequently hydrolyzed to alcohol moieties. Other vinyl polymers which may be useful in the present invention include, but are not limited to, polyvinyl acetate and polyvinyl pyrrolidone. Copolymers such as PVA-methylmethacrylate copolymers or vinyl acetate-vinyl pyrrolidone copolymers (such as Luviskol® VA commercially available from BASF) may also be used in the present invention. PVA is commercially available in a wide range of molecular weights, viscosities and varying degrees of hydrolysis from the polyvinyl acetate precursor. Table A sets forth the parameters for categorizing PVA based on these various characteristics.

TABLE A

Grades of PVA Commercially Available

| Degree of Viscosity | Viscosity Centipoise | Molecular Weight (MW) |
| --- | --- | --- |
| ultra low | 3–5 | 5,000–25,000 |
| low | 5–15 | 25,000–50,000 |
| medium | 15–30 | 50,000–150,000 |
| high | 30–70 | 100,000–200,000 |

TABLE A-continued

Grades of PVA Commercially Available

| Degree of Hydrolysis | % Hydrolysis |
| --- | --- |
| partially | 70–90 |
| intermediately | 90–98 |
| fully | 98–99 |
| super | 99–100 |

Any of the PVAs listed in Table A may be used in the present invention.

The type of PVA used will depend in part on which layer of the granule the PVA is being used in, and will also depend on what characteristics of the granule are to be affected. For example, if PVA is used in the core, it is preferably partially hydrolyzed PVA and low viscosity (low molecular weight) because this will result in lower residue upon dissolution of the granule such as in a washing liquor. The PVA preferred for the enzyme layer is an intermediately, fully or super hydrolyzed PVA with low to medium viscosity. In addition, it is contemplated that mixtures of PVA may be used in any or all layers of the granules of the present invention.

As noted, other vinyl polymers are useful in the present invention including, for example, PVP of varying molecular weights as described in Table B.

TABLE B

Grades of PVP Commercially Available

| Commercial Product | Molecular Weight (Luviskol ® K) |
| --- | --- |
| K-17 | 9,000 |
| K-30 | 45,000 |
| K-60 | 350,000 |
| K-80 | 900,000 |
| K-90 | 1,200,000 -- |

For purposes of toughness of the granule, high MW PVP is preferred, however, from a processing and cost perspective, lower MW polymers (9,000–45,000 MW) are advantageous (while maintaining the performance of the granule).

Additionally, polymers such as polyethylene glycol of MW from about 400–8000, including PEG 3350, can be used. PEG is commercially available from a number of suppliers, including Dow Chemical Company. These polymers, PVP and/or PEG may be preferable when rapid dissolution is required with little or no film forming on the surface of the material coming in contact with the dissolved granule (i.e., dish or glass surface in dishwasher).

Cores

The core particles suitable for use in the present invention are preferably of a highly hydratable material, i.e., a material which is readily dispersible or soluble in water. The core material should either disperse (fall apart by failure to maintain its integrity when hydrated) or solubilize by going into a true aqueous solution. Clays (bentonite, kaolin), nonpareils and agglomerated potato starch are considered dispersible. Nonpareils are spherical particles consisting of a seed crystal that has been built onto and rounded into a spherical shape by binding layers of powder and solute to the seed crystal in a rotating spherical container. Nonpareils are typically made from a combination of a sugar such as sucrose, and a powder such as corn starch. Alternate seed crystal materials include sodium chloride or sulfate seeds and other inorganic salts which may be built up with ammonium sulfate, sodium sulfate, potassium sulfate and the like.

Particles composed of inorganic salts and/or sugars and/or small organic molecules may be used as the cores of the present invention. Suitable water soluble ingredients for incorporation into cores include: sodium chloride, ammonium sulfate, sodium sulfate, urea, citric acid, sucrose, lactose and the like. Water soluble ingredients can be combined with water dispersible ingredients. Cores can be fabricated by a variety of granulation techniques including: crystallization, precipitation, pan-coating, fluid-bed coating, rotary atomization, extrusion, spheronization and high-shear agglomeration.

The cores of the present invention may further comprise one or more of the following: fillers, plasticizers or fibrous materials. Suitable fillers useful in cores of the present invention include inert materials used to add bulk and reduce cost, or used for the purpose of adjusting the intended enzyme activity in the finished granulate. Examples of such fillers include, but are not limited to, water soluble agents such as urea, salts, sugars and water dispersible agents such as clays, talc, silicates, carboxymethyl cellulose or starches.

Suitable plasticizers useful in the cores of the present invention are nonvolatile solvents added to a polymer to reduce its glass transition temperature, thereby reducing brittleness and enhancing deformability. (The glass transition temperature, or Tg, represents the onset of segmental mobility for a polymer.) Typically, plasticizers are low molecular weight organic compounds and are highly specific to the polymer being plasticized. Examples include, but are not limited to, polyols (polyhydric alcohols, for example, alcohols with many hydroxyl radical groups such as glycerol, ethylene glycol, propylene glycol or polyethylene glycol), polar low molecular weight organic compounds such as urea, or other known plasticizers such as dibutyl or dimethyl phthalate, or water.

Suitable fibrous materials useful in the cores of the present invention include materials which have high tensile strength and which can be formed into fine filaments having a diameter of 1 to 50 microns and a length equal to at least four diameters. Typical fibrous materials include, but are not limited to: cellulose, glass fibers, metal fibers, rubber fibers, azlon (manufactured from naturally occurring proteins in corn, peanuts and milk) and synthetic polymer fibers. Synthetics include Rayon®, Nylon®, acrylic, polyester, olefin, Saran®, Spandex® and Vinal®. Typical cellulose fibers would have an average fiber length of 160 microns with a diameter of about 30 microns.

In a granule embodiment of the present invention, the core is a water soluble or dispersible nonpareil (either sugar or salt as described above) which can be further coated by or built up from the seed crystal (nonpareil) using PVA either alone or in combination with anti-agglomeration agents such as titanium dioxide, talc, or plasticizers such as sucrose or polyols. The PVA may be partially hydrolyzed PVA, intermediately hydrolyzed PVA, fully hydrolyzed PVA (all as defined above), or a mixture thereof, with a low to high degree of viscosity. Preferably, the nonpareil is coated with partially hydrolyzed PVA, either alone or in combination with sucrose or such other plasticizer as known in the art. Partially hydrolyzed PVA is preferred because it is believed to result in a lower amount of residue upon dissolution of the granule than fully hydrolyzed PVA. The level of PVA in the coating of the nonpareil may represent from about 0.5% to 20% of the weight of the coated nonpareil. The core of the granules of the present invention, including any coating on such core material as described above, preferably comprises between about 30–85% by weight of the entire coated granule.

In a process embodiment of the present invention, the core material, which may be any material described herein, is charged into the granulator for coating with the first layer, i.e., the enzyme layer.

Enzymes

Any enzyme or combination of enzymes may be used in the present invention. Enzymes are typically coated from relatively impure solutions or slurries in which the active enzyme constitutes only a portion of the total dissolved and suspended solids. Other suspended solids present in the fermentation broth include other proteins, peptides, carbohydrates, other organic molecules and salts. Preferred enzymes include those enzymes capable of hydrolyzing substrates, e.g., stains. These enzymes are known as hydrolases, which include, but are not limited to, proteases (bacterial, fungal, acid, neutral or alkaline), amylases (alpha or beta), lipases, cellulases, and mixtures thereof. Particularly preferred enzymes are subtilisins and cellulases. Most preferred are subtilisins such as described in US RE 34,606, EP Patent 130 756 B1 and EP Patent Application WO 91/06637, which are incorporated herein by reference, and cellulases or cellulase components isolated from *Trichoderma reesei* such as Cellulase 123™ and Multifect™ L250, commercially available from Genencor International, or mixtures thereof, or those described in commonly owned PCT Application PCT/US91/07269 incorporated herein by reference.

The enzyme layer of the present invention contains, in addition to the enzyme per se, a vinyl polymer and preferably PVP. This polymer allows rapid release of the enzyme, while avoiding undesirable residue or filming which is common with many polymers. In a preferred embodiment of the present invention, the enzyme layer comprises PVP of various MW PVP polymers (such as those in Table B above), which PVP is used in an amount of about 0.1–5.0% (preferably 1%) of the granule weight.

The enzyme layer may also further comprise plasticizers and anti-agglomeration agents. Suitable plasticizers useful in the present invention include polyols such as sugars, sugar alcohols or polyethylene glycols (PEGs) having a molecular weight less than 1000, ureas or other known plasticizers such as dibutyl or dimethyl phthalate, or water. Suitable anti-agglomeration agents include fine insoluble material such as talc, $TiO_2$, clays and amorphous silica.

The enzyme layer of the present invention, including any nonenzyme solids and PVP therein, comprises between about 5%–70% by weight of the coated granule.

Coating Layers

The granules of the present invention may comprise one or more coating layers. For example, such coating layers may be one or more intermediate coating layers, or such coating layers may be one or more outside coating layers, or a combination thereof. Coating layers may serve any of a number of functions in a granule composition, depending on the end use of the enzyme granule. For example, coatings may render the enzyme resistant to oxidation by bleach, or coating layers may bring about the desirable rate of dissolution upon introduction of the granule into an aqueous medium, or provide a barrier against ambient moisture in order to enhance the storage stability of the enzyme and reduce the possibility of microbial growth within the granule.

In an embodiment of the present invention, the outer coating layer comprises one or more vinyl polymer(s) and/or one or more polymer(s) and, optionally, a low residue pigment or other excipients such as lubricants. Such excipients are known to those skilled in the art. Furthermore, coating agents may be used in conjunction with other active agents of the same or different categories.

Suitable vinyl polymers include PVA and/or PVP or mixtures of both. If PVA is used, it may be partially hydrolyzed, fully hydrolyzed or intermediately hydrolyzed PVA having low to high degrees of viscosity (preferably partially hydrolyzed PVA having low viscosity). Other vinyl polymers which may be useful include polyvinyl acetate and polyvinyl pyrrolidone. Useful copolymers include, for example, PVA-methylmethacrylate copolymer. Other polymers such as PEG may also be used in the outer layer.

Preferred coatings, particularly for granules needing low dust, rapid dissolution and no filming or residue on surfaces, include a mixture of PVP and PVA or a mixture of PVP and PEG.

The coating layers of the present invention may further comprise one or more of the following: plasticizers, pigments, lubricants such as surfactants or antistatic agents and, optionally, additional enzymes. Suitable plasticizers useful in the coating layers of the present invention are plasticizers including, for example, polyols such as sugars, sugar alcohols or polyethylene glycols (PEGs) having a molecular weight less than 1000, ureas or other known plasticizers such as dibutyl or dimethyl phthalate, or water. Suitable pigments useful in the coating layers of the present invention include, but are not limited to, finely divided whiteners such as titanium dioxide or calcium carbonate, or colored pigments, or a combination thereof. Preferably such pigments are low residue pigments upon dissolution.

As used herein "lubricants" mean any agent which reduces surface friction, lubricates the surface of the granule, decreases static electricity or reduces friability of the granules. Lubricants can also play a related role in improving the coating process, by reducing the tackiness of binders in the coating. Thus, lubricants can serve as anti-agglomeration agents and wetting agents.

In a preferred embodiment of the present invention, from both a granule and processing perspective, the outer coating layer comprises a lubricant. The lubricant reduces attritional dust even further than the coating alone, dramatically decreases processing time and also improves solubility of the granule. It is contemplated that the lubricant added to the outer coating may comprise or replace at least about 30% of the polymer or pigment used in the coating. In a more preferred embodiment, the lubricant is added to the granule as an integral mixture of pigment/polymer/lubricant. As used herein, "integral mixture" means a layer resulting from coating well mixed solutions of the components (pigment/polymer/lubricant) as opposed to the separate addition (layered addition) of each component. As used herein, "pigment" means low residue pigment, such as titanium dioxide, and "polymer" means a polymer, vinyl polymer or copolymer, as defined herein, and preferably PVP, PVA and/or PEG or a mixture thereof.

Suitable lubricating agents include, but are not limited to, surfactants (ionic, nonionic or anionic), fatty acids, antistatic agents and antidust agents. Preferably the lubricant is a surfactant, and most preferably is an alcohol-based surfactant such as a linear, primary alcohol of a 9 to 15 carbon atom chain length alkane or alkene or an ethoxylate or ethoxysulfate derivative thereof. Such surfactants are commercially available as the Neodol® product line from Shell International Petroleum Company. Other suitable lubricants include, but are not limited to, antistatic agents such as StaticGuard™, Downey™, Triton X100 or 120 and the like, antidust agents such as Teflon™ and the like, or other lubricants known to those skilled in the art.

The outer coating layer of the present invention preferably comprises between about 1–20% by weight of the coated granule.

Other Adjunct Ingredients

Adjunct ingredients may be added to the enzyme granules of the present invention. Adjunct ingredients may include: metallic salts, solubilizers, activators, antioxidants, dyes, inhibitors, binders, fragrances, enzyme protecting agents/scavengers such as ammonium sulfate, ammonium citrate, urea, guanidine hydrochloride, guanidine carbonate, guanidine sulfonate, thiourea dioxide, monethyanolamine, diethanolamine, triethanolamine, amino acids such as glycine, sodium glutamate and the like, proteins such as bovine serum albumin, casein and the like, etc., surfactants, including anionic surfactants, ampholytic surfactants, non-ionic surfactants, cationic surfactants and long-chain fatty acid salts, builders, alkalis or inorganic electrolytes, bleaching agents, bluing agents and fluorescent dyes, and caking inhibitors. These surfactants are all described in commonly assigned PCT Application PCT/US92/00384, which is incorporated herein by reference.

The granules described herein may be made by methods known to those skilled in the art of enzyme granulation, including fluidized bed spray-coating, pan-coating and other techniques for building up a granule by adding consecutive layers on top of a starting core material.

The following examples are representative and not intended to be limiting. One skilled in the art could choose other enzymes, cores, particles, methods and coating agents based on the teachings herein.

Experimental

EXAMPLE 1

A batch of PVA/sucrose coated nonpareils was produced by coating a PVA/sucrose solution onto a standard batch of nonpareils. 100 pounds of −25/+40 mesh sucrose/starch nonpareils were charged into a 200 lb capacity coating pan rotating at 45 rpm and heated to a bed temperature of 150° to 170° F. A coating solution was prepared by mixing 112 lbs of an 18% w/w solution of partially hydrolyzed PVA with low viscosity (Airvol 705S, commercially available from Air Products, Inc.) with 144 lbs of a 67% sucrose solution. A total of 38.4 lbs of this unheated mixture were pumped onto the uncoated nonpareils over a period of twelve hours, providing a coating composed of 2.6% w/w PVA and 12.4% w/w sucrose, on the basis of the final product weight. This material was screened to −20/+45 mesh, yielding 101 lbs of usable product and 15 lbs of scrap. A 20 minute Heubach attrition test on 13.5 mgs of coated nonpareil cores (prior to enzyme application) resulted in a total dust reading of 4.2 mg.

In a Glatt GPCG-5 fluidized bed spray-coater, 6300 grams of PVA/sucrose coated nonpareil cores were charged and fluidized to a bed temperature of 44° C. 11.62 kg of protease ultrafiltration concentrate produced from *B. subtilis,* at a concentration of 5.27% w/w protease and 25.7% w/w total solids (such that protease represented 20.5% of total feed concentrate solids), were mixed with a 1.53 kg solution of a 10% w/w fully hydrolyzed PVA with low viscosity (Elvanol 90-50, commercially available from E.I. du Pont de Nemours and Co., Inc.), and 153 grams of amorphous silica (Zeothix 265, commercially available from J.M. Huber Corporation). The enzyme concentrate contained 0.25% sorbitol and 0.5% sodium benzoate as formulation chemicals. This enzyme/PVA mixture was then sprayed onto the fluidized cores at a starting rate of 40 g/minute, ramping up to 110 g/minute over a three hour period, resulting in a weight gain of 3.28 kg. The bed temperature was gradually reduced from 46° to 37° C., and the inlet temperature was held at about 57° to 60° C. over the course of the feed ramp. Atomization air pressure was held at 4.0 bar.

After enzyme application, 7.65 kg of a 40% w/w solution of ammonium sulfate was sprayed onto the granules, at similar conditions to enzyme application, but at an atomization pressure of 3.5 bar. This added another 3.05 kg to the weight of granules. The mass balance of the solids weight gain for these two steps was 99.8%. Finally, a protective coating solution was applied, made by suspending 765 grams of titanium dioxide in 1.147 kg water, then adding 5.10 kg of a 15% partially hydrolyzed PVA with low viscosity (Elvanol 51 -05) stock solution, to provide 6.95 kg of a suspension with net 11 % w/w PVA and 11 % w/w $TiO_2$ concentrations. The coating suspension was sprayed onto the ammonium sulfate coated granule at rates of 50–80 g/minute, an inlet temperature of 63 to 67° C., an outlet temperature of 45° to 49° C., and an atomization air pressure of 4.0 bar. The final product was harvested at 13.285 kg, representing a 78% mass balance for the final coating step, and an overall 89% mass balance for all spray-coating steps. In terms of percent weight gain, the enzyme layer represented a 52% weight gain over the starting core, and the combined three layers represented a 119% weight gain over the core. Product was screened through a 20 mesh screen to remove any agglomerates.

EXAMPLE 2

Two separate lots of an identical enzyme granule formulation were made in a Glatt Uniglatt laboratory fluidized bed spray-coater. Processes for the two lots were virtually identical, so only the second run is described. The starting material was made by charging 595 grams of –20/+50 mesh PVA coated nonpareils into the fluidized bed. These cores were coated by a process similar to that described in Example 1, except that the coating solution consisted of an 18% PVA solution (Airvol 705S) without any sucrose added, and the PVA solution was sprayed onto sucrose/starch nonpareils until the applied PVA coating represented 18% of the weight of the final coated nonpareil mass. (The 18% PVA-coated nonpareils registered 21.0 mg total dust in a Heubach attrition test prior to addition of enzyme.) A 436 gram sample of protease concentrate at a 54 g/kg enzyme concentration and 26.1% total solids concentration was mixed with 94 grams of a 10% PVA (Elvanol 90-50) solution. (Thus, the enzyme represented 20.7% of the total solids in the feed.) The mixture was spray-coated onto the fluidized cores at a rate of 7 g/minute in the Uniglatt, with inlet and outlet temperatures of 55° C. and 45° C., respectively, and an atomization air pressure of 4.0 bar.

Once the enzyme was applied, 588 grams of a 40% ammonium sulfate solution and 539 grams of a suspension containing 11 % PVA (Elvanol 51-05) and 11% $TiO_2$ were applied under similar process conditions, with coating rates of 17 g/minute and 7 g/minute, respectively. The final product weighed 1023 grams, prior to sieving, a 90% yield on overall solids gain. This represents a net weight gain over the core weight of about 18% for the enzyme layer and about 72% overall. Product was sieved between 20 and 50 mesh screens to remove agglomerates and fines.

Example 1 and Lot 2 of Example 2 were subjected to several tests and compared with a comparable commercial product, Savinase 6.OT (available from Novo Nordisk Industri A/S). In a Heubach attrition test, using a fill volume of about 17 cc in a 20 minute test time with an airflow rate of 20 liters per minute desiccated air, the following comparative dust levels were obtained:

|  | Total dust (mg) | Enzyme dust (mg) |
| --- | --- | --- |
| Savinase | 5.7 | 24 |
| Example 1 | 0.6 | 7 |
| Example 2, Lot 2 | 0.6 | 4 |

In a test for potential residue left by enzyme granules after a standard wash cycle at 60° F., Savinase 6.OT left a fine white residue on the cloth, indicating the presence of some insolubles. Examples 1 and 2 left equivalent or lower levels of residue than Savinase 6.OT.

Figure 3:
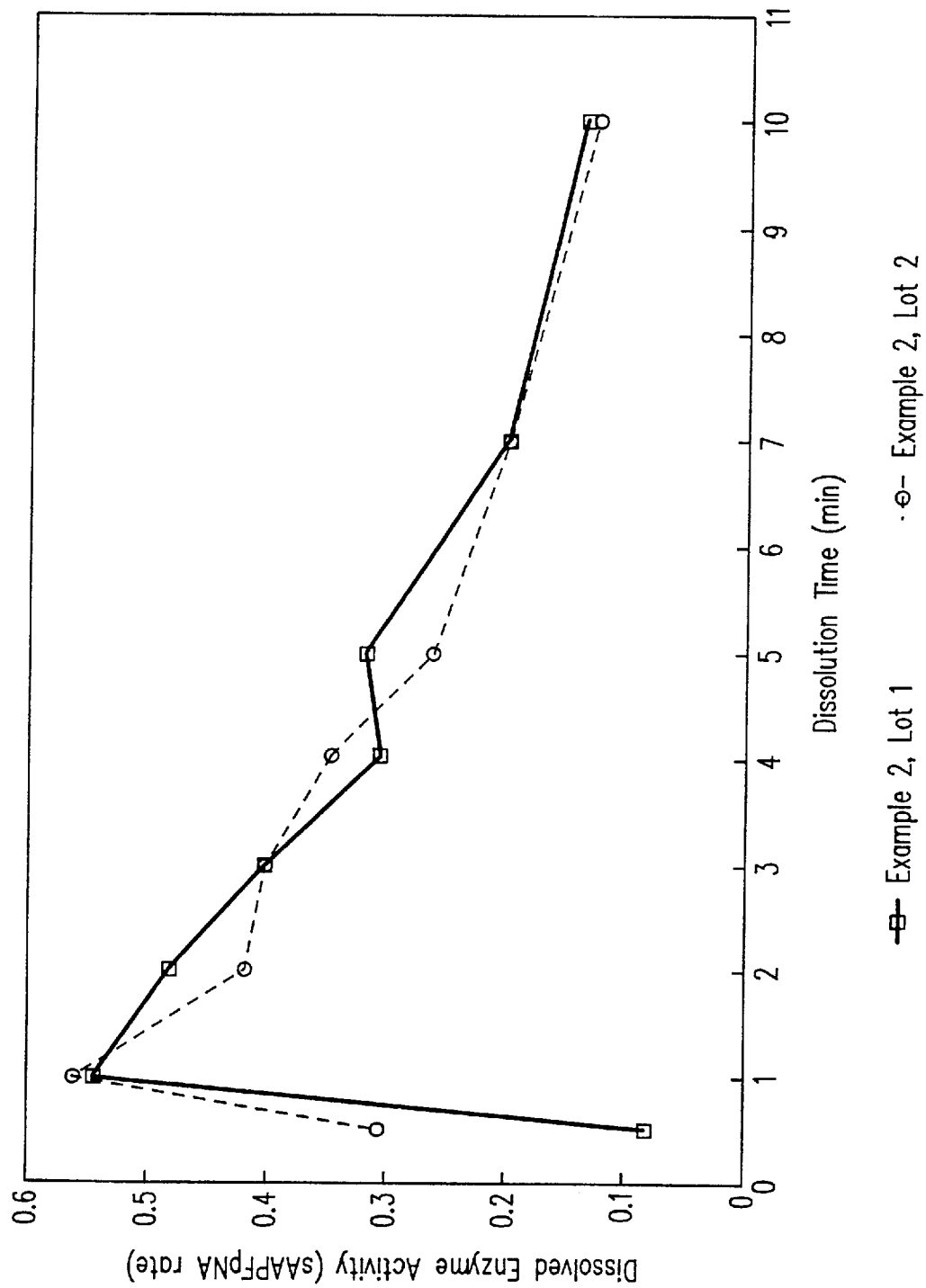
FIG. 3 is a graph showing dissolution profiles of certain enzyme granules.
Figure 4:
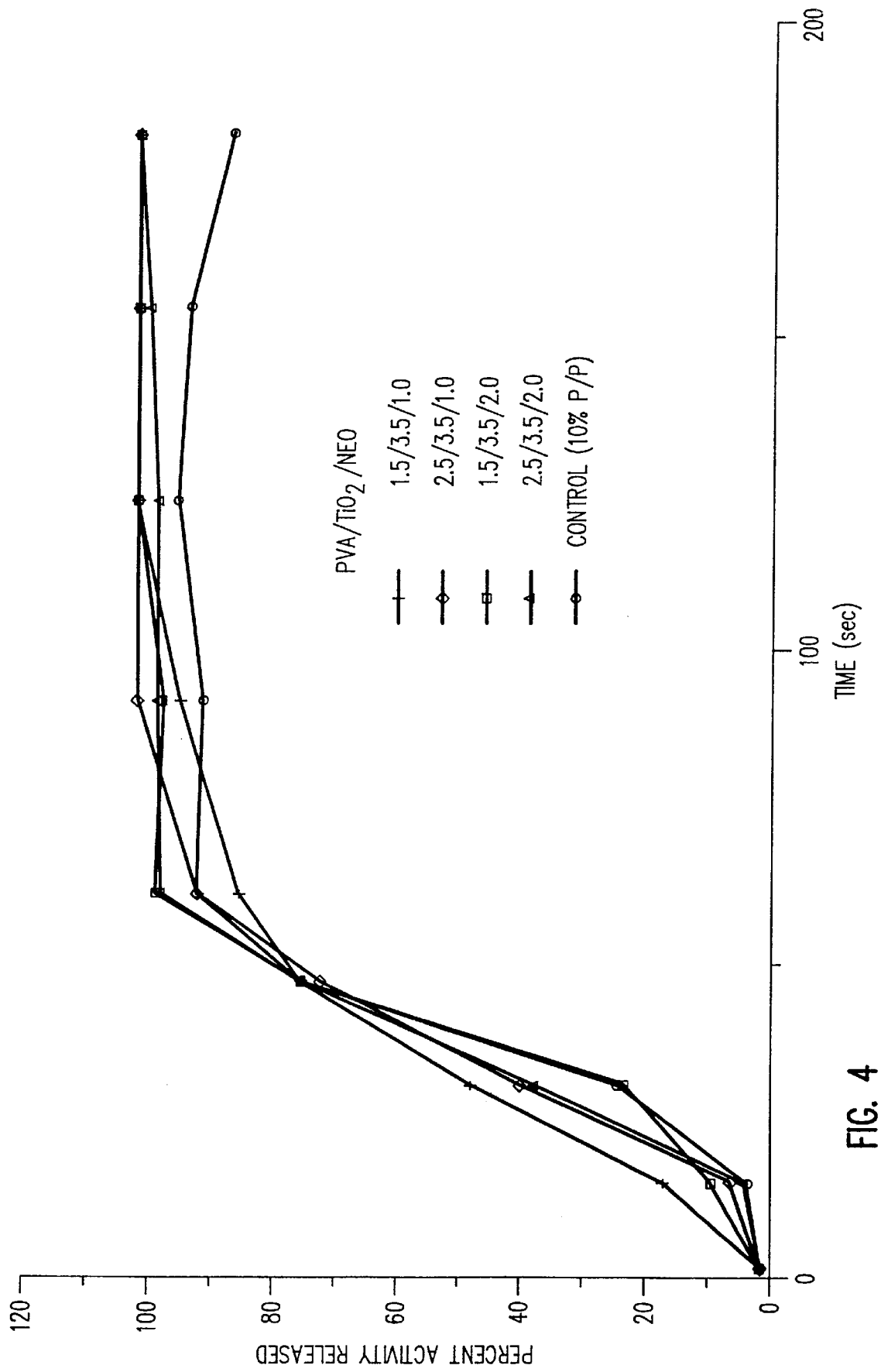
FIG. 4 shows dissolution profiles of enzyme granules comprising various ratios of polymer:pigment and polymer:pigment:lubricant.

Dissolution profiles indicating rates of enzyme release under realistic detergent conditions are shown in FIG. 3 for both lots of Example 2. These profiles were generated in a dissolution tester with detergent present at 120° F., 10 grains per gallon hardness and a fixed medium stir rate. Activities were measured using a synthetic substrate rate assay. Even at these high temperatures, it can be seen that the rate of enzyme release is delayed. This can be an advantage in that it allows time for scavenging of residue wash water chlorine by the ammonium sulfate in the granule and protein materials released from the clothing. The delay also protects the enzyme against high temperature autolysis until released proteins and peptides are available to inhibit autolysis via peptide inhibition.

EXAMPLE 3

A granulated cellulase for textile applications was produced in a Uniglatt spray-coater. 842 grams of –30/+50 mesh regular sucrose/starch nonpareils were charged into the coater and fluidized at a bed temperature of 42° to 48° C. A 321 gram solution of cellulase ultrafiltration concentrate from *T. reesei*, containing 6% w/w protein and 21 % w/w total solids, was mixed with a 235 gram solution of 10% fully hydrolyzed PVA (Airvol 107). This mixture was sprayed onto the fluidized nonpareils at a rate of about 9 g/minute, resulting in a weight gain of 88 grams, or about 10.5% w/w. Over the enzyme/PVA layer, 275 grams of a coating suspension containing 12.7% PVA (Airvol 205) and 12.7% $TiO_2$ was sprayed on, bringing the total granule weight to 1000 grams, a total weight gain of 18.8%. Of the final granule, 6.0% w/w was cellulase protein.

In comparison with a competitive product, Denimax Acid T (commercially available from Novo Nordisk Industri A/S), Example 3 had identical total Heubach dust, 25 mg in both cases. The polyvinyl alcohol binder and coating provided the granule of Example 3 with superior stability of the cellulase activity at high temperature and high humidity.

The cellulase granules produced in this example were evaluated for storage stability in comparison with a commercial product, Denimax Acid T (Novo Nordisk Industri A/S). The amount of residual activity measured after storage for eight days at 37° C., at low and high relative humidity was as follows:

|  | Relative Humidity (R.H.) | |
| --- | --- | --- |
|  | Residual Activity at 0% R.H. | Residual Activity at 60% R.H. |
| Example 3 | 117 | 112 |
| Denimax Acid T | 102 | 26 |

Thus, the use of polyvinyl alcohol in the enzyme layer, and especially in the outer coating, confers excellent protection against the destabilizing effects of high temperature in combination with high humidity.

EXAMPLE 4

A granulated detergent lipase was produced in the Uniglatt spray-coater. 456 grams of the PVA/sucrose coated nonpareils described in Example 1 were charged into the reactor. 1.882 liters of a lipase ultrafiltration concentrate containing 10 g/L enzyme and 16.5% w/w total solids was sprayed onto the cores without admixed PVA. Inlet and outlet temperatures averaged 60° and 45° C., respectively, allowing a coating rate of about 8 g/minute at 4 bar atomization. A 432 gram suspension of 11 % w/w PVA (Elvanol 51-05) and 11 % w/w $TiO_2$ was sprayed onto the lipase coated cores. The lipase application added 307 grams to the cores, a 67% weight gain. The final product weight was 808 grams, prior to screening, a net 77% weight gain. A Heubach attrition test yielded a total dust level of 0.8 mg; no measurement of active lipase dust content was available.

EXAMPLE 5

A granulated detergent protease was produced in a Glatt fluidized bed spray-coater substantially as described in Examples 1 and 2; however, the outer coating formulation applied to the granulation product was an integral mixture of $TiO_2$/PVA/Neodol® in quantities provided below:

|  | kg | Solution % | Dry Weight On Granule % |
| --- | --- | --- | --- |
| $TiO_2$ | 47.5 | 11.0 | 5 |
| PVA (51-05) | 38.0 | 8.8 | 4 |
| Neodol® | 9.5 | 2.2 | 1 |
| Water | 337.0 | 78.0 | 0 |
|  | 432.0 | 100.0 |  |

The $TiO_2$/PVA/Neodol® coating mixture described above was applied to 684 kg of uncoated product at a 10% level to yield 760 kg of final product. The coating was applied at a maximum spray rate of about 1.6 kg/min.

The overall coating time for application of this coating mixture was measured and compared to the overall coating time for previous examples (particularly Example 1) where a 50—50% mixture of PVA/$TiO_2$ and 0% Neodol® were used. Such comparison showed that coating time was reduced by about 50% when a surfactant was incorporated in the coating mixture as compared to coating time for a pigment/polymer layer only.

The total dust for the product of Example 5 was 0.6 mg/13.5 g of product, as measured by the Heubach dust assay referred to in Example 2. Product wash performance and solubility were similar to Examples 1 and 2.

EXAMPLE 6

Following procedures substantially as described in Examples 1–3, three granulated cellulase and protease containing products were produced in a Uniglaft spray-coater.

The three experimental lots comprised the following compositions, coated on nonpareil core materials:

| Exp. # | Active Cellulase (%) | Protease Protease (%) | Surfactant (wt %) | Pigm/Polym (wt %) |
| --- | --- | --- | --- | --- |
| A | 6.5 | 0.56 | 4.49 | 3.67 |
| B | 6.5 | 0.52 | 0 | 3.14 |
| C | 6.5 | 0.59 | * | 6.11* |

*Surfactant suspended in polymer coating; therefore, total polymer and surfactant shown in Pigment/Polymer column In Experiment A, the non-enzyme coating comprised individual applications of pigment/polymer, $TiO_2$/PVA (Elvanol 51-05), and surfactant (Triton X120). Experiment B utilized no surfactant, only a pigment/polymer coating of $TiO_2$/PVA (Elvanol 51-05). In Experiment C, the non-enzyme coating comprised surfactant suspended in the polymer; thus, the coating in this experiment was Triton X120/ Elvanol 51-05.

The three experimental lots (A, B and C) were tested for total dust level in the Heubach test referred to in Example 2. The following comparative dust levels were obtained:

| Exp # | Average dust (mg)/13.5 g |
| --- | --- |
| A | 42.5 |
| B | 255.0 |
| C | 4.2 |

These results show that the distinct surfactant layer of Experiment A seems to lower dust; however, a more dramatic effect of lowering dust is evidenced when the surfactant is suspended in the PVA forming an integral mixture (see Experiment C).

In addition to lowering dust levels, it was observed that the addition of the surfactant as an integral mixture of the PVA coating layer, enhanced feed rate; thus reducing the total processing time, as compared to feed rate for normal pigment/polymer coatings (without surfactant).

Granules made as described herein have improved dust characteristics when compared to other granules known in the art. These improved dust characteristics are achieved while other desirable characteristics of the granules, such as solubility, stability, delayed release and low residue, are maintained or improved. In addition, in certain embodiments of the present invention (i.e., Example 5), feed rate may be enhanced with resulting reduction in coating time without adversely affecting the desirable characteristics of the claimed granules. Thus, cost may be reduced while enhancing product characteristics.

EXAMPLE 7

17.8 kg of an alkaline protease solution of 15% solids was spray coated onto 15.5 kg of PVA coated non-pareils using a Glatt GPGC-5 fluidized bed such that the final product contained 4% activity by weight. Included with the enzyme solution was low molecular weight PVP (Luviskol K-17 commercially available from BASF) in an amount such that the final product contained 1 % by weight. It was applied with an inlet temperature between 82°–92° C. and an exhaust temperature of 50°–60° C. An atomizing air pressure of 3.5 bar was utilized throughout the process. After all of the solutions were applied, water was sprayed and the product was dried to completion.

1.01 kg of the previous material was coated with 1.2 kg of a 30% solution of sodium sulfate using a Vector FL-1 fluidized bed machine. This solution was applied such that a 20% final product weight was sodium sulfate. It was spray coated with an inlet temperature between 70°–85° C. and an exhaust temperature of 40°–50° C. 50 psi atomizing air pressure was maintained throughout the process. When the solution was finished, a small amount of water was applied and the product dried to completion.

Again in the Vector FL-1, 0.9 kg of solution containing 12.5% titanium dioxide, 7.6% low molecular weight PVP (Luviskol K-17), 2.5% polyethylene glycol (MW=3350) and 1.2% Neodol 23-6.5 was applied. The solution was applied such that the final product contained 13.3% by weight of the solids. An inlet temperature of 55°–62° C. and an exhaust temperature of 38°–41° C. were maintained. 50 psi atomizing air pressure was utilized. After the solution was applied, a small amount of water was sprayed and the product was dried to completion.

To this a 10% Neodol 23-6.5 solution was applied such that the final product weight was 0.25% by weight. The solution was applied with an inlet temperature between 60°–65° C. and an exhaust temperature of 40°–50° C. After application of the Neodol solution, a small amount of water was applied and the product was dried to completion.

The end product was then sieved through US standard 20 and 50 mesh screens. 99.9% of the product was contained in this fraction. The resulting product was tested for dust levels utilizing a Heubach Type III dustmeter. 13.5 grams of product was tested using a air flow rate of 200 deca liters per minute for twenty minutes. The level of active enzyme dust liberated was measured by dissolving the dust in buffer and detecting activity using synthetic AAPF substrate. The active dust level obtained was 31.99 ug per 13.5 g sample.

EXAMPLE 8

55 kg of a protease solution of 15% solids was spray coated onto 25 kg of PVA coated non-pareil using a Vector FL-60 fluidized bed such that the final product contained 4% activity by weight. Included with the enzyme solution was low molecular weight PVP (Luviskol K-17) in an amount such that the final product contained 1% by weight. The enzyme with PVP was applied with an inlet temperature between about 80°–95° C. and an exhaust temperature of between about 65°–70° C. An atomizing air pressure of 75 psi was utilized throughout the process. When all of the solution was applied, water was sprayed and the product was dried to completion.

To this, 37 kg of a 30% solution of sodium sulfate was added. This solution was applied such that a 20% final product weight was sodium sulfate. It was spray coated with an inlet temperature between about 35°–60° C. and an exhaust temperature of between about 35°–55° C. Again, 75 psi atomizing air pressure was maintained. When the solution was finished a small amount of water was applied and the product dried to completion.

To this, 33 kg of a solution containing 9.4% titanium dioxide, 7.5% low molecular weight PVP (Luviskol K-17), 2.5% partially hydrolyzed polyvinyl alcohol and 2.5% Neodol 23-6.5 was applied. The solution was applied such that the final product contained 11.6% by weight of the solids. An inlet temperature of between about 54°–56° C. and an exhaust temperature of between about 38°–44° C. were maintained. 75 psi atomizing air pressure was utilized. Once all of the solution was applied, a small amount of water was sprayed and the product was dried to completion.

To this a 10% Neodol 23-6.5 solution was applied such that the final product weight was 0.5% by weight. The solution was applied with an inlet temperature between about 55°–60° C. and an exhaust temperature of between about 40°–45° C. When the solution was finished, a small amount of water was applied and the product was dried to completion.

The end product was then sieved through US standard 20 and 50 mesh screens. 94% of the product was contained in this fraction. The resulting product was tested for toughness utilizing a Heubach Type IIII dustmeter as in Example 7. The active dust level obtained was 0.65 ug per 13.5 g sample.

What is claimed:

1. An enzyme-containing granule comprising:
   a) a core comprising a water soluble or dispersible material coated with a polyvinyl alcohol or copolymer thereof;
   b) an enzyme layer comprising one or more enzyme(s) and polyvinyl pyrrolidone; and
   c) an outer coating layer comprising one or more polymer(s) selected from the group consisting of polyvinyl pyrrolidone, polyvinyl alcohol and polyethylene glycol.

2. A granule of claim 1 wherein the polyvinyl alcohol useful in the core is partially hydrolyzed.

3. A granule of claim 1 wherein the core comprises a salt or sugar nonpareil.

4. A granule of claim 3 wherein said nonpareil is coated or built up with partially hydrolyzed polyvinyl alcohol.

5. A granule of claim 1 wherein the enzyme layer comprises one or more enzyme(s) selected from the group consisting of protease, amylase, lipase, cellulase, xylanase, oxidase, peroxidase and mixtures thereof.

6. A granule of claim 5 wherein the enzyme layer further comprises:
   a) a plasticizer; or
   b) an anti-agglomeration agent.

7. A granule of claim 1 wherein the outer coating comprises a mixture of polyvinyl pyrrolidone and polyvinyl alcohol or a mixture of polyvinyl pyrrolidone and polyethylene glycol.

8. A granule of claim 1 wherein the outer coating layer (c) further comprise s a low residue pigment.

9. A granule of claim 8 wherein the pigment is titanium dioxide.

10. A granule of claim 1 wherein the outer coating layer (c) further comprises a lubricant.

11. A granule of claim 10 wherein the lubricant is a nonionic or anionic surfactant.

12. A granule of claim 11 wherein the surfactant is a linear primary alcohol of a 9–15 carbon atom chain length alkane or alkene or an ethoxylate or ethoxysulfate derivative thereof.

13. An enzyme-containing granule comprising:
   a) a nonpareil core;
   b) an enzyme layer comprising one or more enzyme(s) and polyvinyl pyrrolidone; and
   c) an outer coating layer comprising a mixture of polyvinyl alcohol and polyvinyl pyrrolidone or a mixture of polyvinyl pyrrolidone and polyethylene glycol.

14. A granule of claim 13 further comprising a low residue pigment in the outer coating.

15. A granule of claim 14 further comprising a lubricant in the outer coating.

16. A granule of claim 15 wherein the lubricant is a nonionic or ionic surfactant.

17. A granule of claim 16 wherein the surfactant is a linear primary alcohol of 9–15 carbon atom chain length alkane or alkene or an ethoxylate or ethoxysulfate derivative thereof.

18. An enzyme-containing granule comprising:

a) a nonpareil sugar or salt core coated with partially hydrolyzed polyvinyl alcohol having low viscosity;

b) an enzyme layer comprising one or more enzyme(s) and polyvinyl pyrrolidone; and c) an outer coating layer comprising a mixture of partially hydrolyzed polyvinyl alcohol and polyvinyl pyrrolidone, a low residue pigment and a linear primary alcohol of 9–15 carbon atom chain length alkane or alkene, or an ethoxylate or ethoxysulfate derivative thereof.

19. An enzyme-containing granule comprising:

a) a nonpareil sugar or salt core coated with partially hydrolyzed polyvinyl alcohol having low viscosity;

b) an enzyme layer comprising one or more enzyme(s) and polyvinyl pyrrolidone; and c) an outer coating layer comprising a mixture of polyvinyl pyrrolidone and polyethylene glycol, a low residue pigment and a linear primary alcohol of 9–15 carbon atom chain length alkane or alkene, or an ethoxylate or ethoxysulfate derivative thereof.

20. A method for making an enzyme-containing granule, said method comprising:

a) selecting a suitable core material;

b) coating the core of step a) with an enzyme layer comprising one or more enzyme(s) and polyvinyl pyrrolidone; and c) coating the product of step b) with one or more of polyvinyl alcohol, polyvinyl pyrrolidone and polyethylene glycol, alone or in combination with one or more pigment(s), lubricant(s), or a mixture thereof.

* * * * *